US011085919B2

(12) United States Patent
Manganini et al.

(10) Patent No.: US 11,085,919 B2
(45) Date of Patent: Aug. 10, 2021

(54) METHOD FOR DETECTING CHEMICAL SUBSTANCES IN SAMPLES OF MATERIAL THAT CAN BE TAKEN FROM A SUBJECT, IN PARTICULAR FOR DETECTING EMBRYOTOXIC FACTORS

(71) Applicant: GEXNANO S.R.L., Gerenzano (IT)

(72) Inventors: Massimiliano Manganini, Mozzate (IT); Renato Colognato, Ispra (IT); Massimo Mariotti, Legnano (IT); Alessandro Scozzesi, San Zeno Naviglio (IT)

(73) Assignee: INNOVITAS VITAE S.R.L., Brescia (IT)

(*) Notice: Subject to any disclaimer, the term of this patent is extended or adjusted under 35 U.S.C. 154(b) by 106 days.

(21) Appl. No.: 16/151,516

(22) Filed: Oct. 4, 2018

(65) Prior Publication Data
US 2019/0033298 A1 Jan. 31, 2019

Related U.S. Application Data

(63) Continuation of application No. 14/895,416, filed as application No. PCT/IB2013/060334 on Nov. 22, 2013, now abandoned.

(30) Foreign Application Priority Data

Jun. 4, 2013 (IT) .......................... MI2013A000916

(51) Int. Cl.
*G01N 33/50* (2006.01)
*G01N 33/68* (2006.01)

(52) U.S. Cl.
CPC ..... *G01N 33/5088* (2013.01); *G01N 33/5091* (2013.01); *G01N 33/689* (2013.01); *G01N 2800/368* (2013.01)

(58) Field of Classification Search
CPC ......... G01N 2800/368; G01N 33/5088; G01N 33/5091; G01N 33/689
See application file for complete search history.

(56) References Cited

FOREIGN PATENT DOCUMENTS

WO 9428425 A1 12/1994

OTHER PUBLICATIONS

Padilla: "Toxicity Screening Using Zebrafish Embryos: Form and Function", Reproductive Toxicology; Sep. 26, 2012; XP055100365; 36 pages.
Selderslaghs, et al., "Feasibility Study of the Zebrafish Assay as an Alternative Method to Screen for Developmental Toxicity and Embryotoxicity Using a Training Set of 27 Coumpounds", Reproductive Toxicology, Aug. 17, 2011; vol. 33, No. 2, pp. 142-154; 2011.
Padilla, et al., "Zebrafish Developmental Screening of the ToxCast Phase I Chemical Library", Reproductive Toxicology, Dec. 9, 2011; vol. 33, No. 2, pp. 174-187; 2011.
Sukardi, et al., "Expert Opinion in Drug Metabolism and Toxicology"; vol. 7, No. 5; pp. 579-589; 2011.
Ingrid W.T. Selderslaghs, An R. Van Rompay, Wim De Coen, Hilda E Witters, "Development of a screening assay to identify teratogenic and embryotoxic chemicals using the zebrafish embryo", Reproductive Toxicology, (2009), pp. 308-320, vol. 28 Elsevier Inc.
Kimberly C. Brannen, Julieta M. Panzica-Kelly, Tracy L. Danbery, and Karen A. Augustine-Rauch, "Development of a Zebrafish Embryo Teratogenicity Assay and Quantitative Prediction Model", Birth Defects Research (Part B) Dev Reprod. Toxicol., Feb. 2010, pp. 66-77, vol. 89(1), Wiley-Liss, Inc.
Julieta M. Panzica-Kelly, Cindy X. Zhang, Tracy L. Danberry, Annette Flood, Judiann W. Delan, Kimberly C. Brannen, and Karen A. Augustine-Rauch, "Morphological Score Assignment Guidelines for the Dechorionated Zebrafish Teratogenicity Assay", Birth Defects Research (Part B) Dev Reprod Toxicol., Oct. 2010, pp. 382-395, vol. 89(5), Wiley-Liss, Inc.
Karen Augustine-Rauch, Cindy X. Zhang, and Julieta M. Panzica-Kelly, "In Vitro Developmental Toxicology Assays: A Review of the State of the Science of Rodent and Zebrafish Whole Embryo Culture and Embryonic Stem Cell Assays", Birth Defects Research (Part C) Embryo Today., Jun. 2010, pp. 87-98, vol. 90(2), Wiley-Liss, Inc.
Stefan Weigt, Nicole Huebler, Ruben Strecker, Thomas Braunbeck, Thomas H. Broschard, "Zebrafish (*Dania rerio*) embryos as a model for testing proteratogens", Toxicology, Mar. 15, 2011, pp. 25-36, vol. 281 (1-3), Elsevier Ireland Ltd.
Kathleen Van Den Bulck, Adrian Hill, Natalie Mesens, Heike Diekman, Luc De Schaepdrijver, Lieve Lammens, "Zebrafish developmental toxicity assay: A fishy solution to reproductive toxicity screening, or just a red herring?", Reproductive Toxicology, Sep. 2011, pp. 213-219, vol. 32(2), Elsevier Inc.
A.-L. Gustafson, D.B. Stedman, J. Ball, J.M. Hillegass, A. Flood, C.X. Zhang, J. Panzica-Kelly, J. Cao, A. Coburn, B.P. Enright, M.B. Tornesi, M. Hetheridge, K.A. Augustine-Rauch, "Inter-laboratory assessment of a harmonized zebrafish developmental toxicology assay—Progress report on phase I", Reproductive Toxicology. Apr. 2012, pp. 155-164, vol. 33(2), Elsevier Inc.

(Continued)

Primary Examiner — Blaine Lankford
(74) Attorney, Agent, or Firm — Pearne & Gordon LLP

(57) ABSTRACT

A method for detecting chemical substances in samples of material that can be taken from a subject, comprising a step of preparing a sample of a substance coming from a donor organism; a step of associating with said sample of a substance a control element suitable for verifying a presence of at least one active agent in the sample of the substance and a step of verifying the presence or absence of the active agent based on a change in state in said control element; the control element comprising at least one living organism having the ability to nourish itself autonomously through temporary organs associated with the living organism itself and able to supply nutritive substances to the latter without taking said nutritive substances from an outside environment.

12 Claims, No Drawings

(56) References Cited

OTHER PUBLICATIONS

E. Teixidó, E. Piqué, J. Gómez-Catalán, J..M. Llobet, "Assessment of developmental delay in the zebrafish embryo teratogenicity assay", Toxicology in Vitro, Feb. 27, 2013, pp. 469-478, vol. 27(1), Elsevier Ltd.

Lien T. H. Nguyen, Colin R. Janssen, "Comparative Sensitivity of Embryo-Larval Toxicity Assays with African Catfish (*Clarias gariepinus*) and Zebra Fish (*Danio rerio*)", Environmental Toxicology, 2001, pp. 566-571, vol. 16 (6), John Wiley & Sons, Inc.

Julieta M. Panzica-Kelly, Cindy X. Zhang, and Karen Augustine-Rauch, "Zebrafish Embryo Developmental Toxicology Assay", Methods in Molecular Biology, 2012, pp. 25-50, vol. 889, Chapter 4, Springer Science+Business Media, LLC.

Evyn Loucks, Michael J. Carvan III, "Strain-dependent effects of developmental ethanol exposure in zebrafish", Neurotoxicology and Teratology, Nov.-Dec. 26, 2004, pp. 745-755, vol. 26(6), Elsevier Inc.

Uwe Strahle, Stefan Scholz, Robert Geisler, Petra Greiner, Henner Hollert, Sepand Rastegar, Axel Schumacher, Ingrid Selderslaghs, Carsten Weiss, Hilde Witters, Thomas Braunbeck, "Zebrafish embryos as an alternative to animal experiments—A commentary on the definition of the onset of protected life stages in animal welfare regulations", Reproductive Toxicology, Apr. 2012, pp. 128-132, vol. 33(2), Elsevier Inc.

Kelly Selman, Robin A. Wallace, Andrew Sarka, and Xiaoping Qi, "Stages of Oocyte Development in the Zebrafish, *Brachydanio rerio*", Journal of Morphology, Nov. 1993, pp. 203-224, vol. 218(2), Wiley-Liss, Inc.

Lara Carvalho and Carl-Philipp Heisenberg, "The yolk syncytial layer in early zebrafish development", Trends in Cellular Biology, Oct. 2010, pp. 586-592, vol. 20(10), Elsevier Ltd.

Lisa Truong, Stacey L. Harper, and Robert L. Tanguay, "Evaluation of Embryotoxicity Using the Zebrafish Model", Methods in Molecular Biology, 2011, pp. 271-279, vol. 691, Chapter 16, Springer Science+Business Media, LLC.

Shaukat Ali, Harald G. J. Van Mil, Michael K. Richardson, "Large-Scale Assessment of the Zebrafish Embryo as a Possible Predictive Model in Toxicity Testing", PLoS One, Jun. 2011, pp. 1-10, vol. 6(6), e21076.

METHOD FOR DETECTING CHEMICAL SUBSTANCES IN SAMPLES OF MATERIAL THAT CAN BE TAKEN FROM A SUBJECT, IN PARTICULAR FOR DETECTING EMBRYOTOXIC FACTORS

The present invention relates to a method for detecting, in samples of material that can be taken from a subject (who can be, for example, a woman in fertile age), one or more chemical substances which can exert different effects, such as a harmful effect on the growth or maintenance of the viability of an embryo.

As is known from the clinical statistics available today, approximately 40% of patients affected by phenomena of recurrent miscarriage with no ascertained cause are characterized by the presence of so-called "embryotoxic factors" (abbreviated with the acronym ETFs) in their blood: these factors are a set of molecules correlated with a biological mechanism whereby during the implantation stage or during the earliest stages of pregnancy, the embryo is mistakenly considered a foreign object in the future mother's body, which develops a specific immune response with the aim of eliminating it.

Also known from recent clinical studies is the correlation between the presence of ETFs in the mother's body and a non-negligible number of cases of idiopathic infertility (or even cases of sterility mistakenly attributed to so-called endometriosis), and this is indicative of the central role of ETFs as "markers" of various clinical risk situations.

In other words, it is of fundamental importance to implement systems for diagnosing ETFs, so as to be able to predict difficulties in embryo implantation and/or the occurrence of miscarriages or anything else in advance: in this regard, the prior art available today (still considered at an experimental stage) envisages the use of mouse embryos or live cell cultures.

Irrespective of the type of test media utilizable, the known methods use a blood sample of a patient, from which the white cells are extracted and then cultured in the presence of embryonic factors that ensure their activation (or, in other words, stimulate an immune response), and subsequently the so-called "conditioned medium" (abbreviated in laboratory jargon as CM) obtained from the extraction/activation of white blood cells is placed in contact with the organic substances used for analysis (for example, if mouse embryos are used, the latter are observed for three days after being incubated with the CM).

Following this exposure, if the embryos die, it is deduced that toxic substances are present in the patient's serum (these in general fall within the definition of ETFs), whereas if, on the contrary, the embryos develop normally, the test is negative.

Alternatively, the CM is incubated with a JEG-3 type cell culture and the level of cell mortality is evaluated after three days (this level is considered indicative of the presence of ETFs).

The methods for verifying the presence of ETFs summarized above have several substantial disadvantages, particularly in terms of operating costs, speed of execution of the protocol and hence of production of results, low statistical "robustness" and operational flexibility: in particular, the choice of a "biological material" (mouse embryos or JEG-3 cells) to react the culture medium with implies operational complications, both from a cost standpoint and in terms of the growth/culture/development of the test organic material itself.

Moreover, the use of "animal models" in the known test processes could lead to a problem of an ethical type, given the growing attention/aversion of the media and public opinion precisely toward the use of animal models in clinical trial processes: in the case of tests to identify ETFs (tests that have evident diagnostic purposes), a possible limitation/abolition "by law" of animal models in this type of testing as well would lead, in fact, to a nearly complete impossibility of carrying them out, also given that such tests for identifying ETFs cannot be considered like tests performed under clinical trial conditions (where the use of animal models may and may continue to be allowed), as they are veritable diagnostic tests.

The object of the present invention is thus to conceive a method for detecting substances, and in particular toxic substances, such as, for example, ones tied to the definition of ETFs, which overcomes the disadvantages of the prior art.

In particular, it is an object of the present invention to implement a method that minimizes operating costs, provides a large amount of material to be exposed to the possible presence of ETFs and thus makes it possible to carry out a large number of tests (possibly also of a recursive or parallel type on samples taken from the same subject) with excellent qualitative and quantitative reliability in terms of results.

These and other objects of the invention are achieved with a method illustrated here below, in a non-limiting example embodiment thereof, as well as in one or more of the appended claims.

The method substantially comprises the typical steps of a laboratory test procedure, namely:
  preparing a sample of a substance (which can typically comprise organic fluids and/or portions of tissues originating from the body of a donor);
  associating with the sample of a substance a control element suitable for verifying a presence of at least one active agent in the sample of the substance; and
  verifying a presence or absence of the active agent based on a change in state (physical, chemical or biological) in the control element, Advantageously, the present method envisages that the control element comprises at least one living organism having the ability to nourish itself autonomously through temporary organs associated with the living organism itself and able to supply nutritive substances to the latter, that is, without taking them from an outside environment.

The particular definition of this property of the control element in accordance with the present invention makes it possible to use an organism with a sufficient degree of tissue and systemic development, such that from a regulatory standpoint the material is not considered "animal", but only a "biological material", and thus does not fall within the area (that of experimentation) which is regulated by legislation on tests with animals: this will be better explained further below in the present description.

Going into detail, one can see how the living organism selectable in accordance with the present method can comprise at least a fish belonging to the class of Actinopterygii, and typically the species called *Danio rerio* (also known by the common name "zebrafish"): in even further detail, one can choose a *Danio rerio* belonging to the "AB" type genotypic strain.

Alternatively, the present method can be implemented by choosing a fish of the species *Oryzias latipes* (also known by the common name "Japanese rice fish" or by the name "medaka") as the living organism for performing tests and analyses.

Or, as an alternative to the models described above, the class of amphibians including the genus *Xenopus*.

According to a particular feature of the present invention, the possible organisms (such as, for example, the two fish and the amphibian presented above) will be used in their biological form in which they are able to nourish themselves autonomously by means of a temporary organ referred to in jargon as "yolk sac" (otherwise called simply yolk according to current English scientific terminology) or similar temporary organs that have developed integrally with the living organism itself: if fish of the species *Danio rerio* are used, this is possible until the living organism reaches a lifetime less than or equal to 120 hours of development after fertilization (at a standard temperature), whereas in the case in which fish of the species *Oryzias latipes* are used, this is possible until the living organism reaches a lifetime less than or equal to 288 hours of development after fertilization. In the case of *Xenopus*, the larval stage is aquatic and the yolk is preserved for up to about 96 hours of development after fertilization. After this stage it draws nourishment from the outside. *Xenopus* is considered by the EU to be an official experimental animal model.

At this point it should be noted that upon exceeding this time threshold, the embryo of *Danio rerio* (or *Oryzias latipes* or *Xenopus*, depending on the cases) uses up all the nutrients present in its yolk sac and becomes dependent on the outside environment from a nutritional viewpoint: from this moment on it is considered an animal from a regulatory viewpoint and is consequently subject to legislation on animal experimentation (which entails considerable increases in operating costs and in costs of executing laboratory tests on a large scale).

From a practical viewpoint, the step of associating a control element with the sample of a substance comprises the following sub-steps:
  first, a predetermined number of living organisms is exposed to the sample of the substance taken (for example, one may consider at least 20 embryos of *Danio rerio* having a development time of no more than 72 hours after fertilization);
  equal groups of embryos (of *Danio rerio* or *Oryzias latipes* or *Xenopus*, for example two groups of 10) are placed in a specific culture medium in suitable verification containers, which can be, for example, two adjacent wells of a culture plate (which can in turn comprise 24 wells); and
  the sample of the substance, which can typically be a blood serum taken from a donor subject, is added to the culture medium just mentioned at a suitable concentration.

As regards the execution of the step of verifying the presence/absence of the active agent, it should be noted that this can conveniently be designed to verify an absence/presence of so-called "embryotoxic factors (ETFs)" and comprise the following sub-steps:
  an environmental interaction is maintained, typically in the wells of the culture plate, between the embryos and the sample of the substance for a period of interaction defined as twelve hours (or in any case multiples of twelve hours, up to a maximum of 48 hours);
  a number of deceased embryos is counted after the just mentioned twelve hours and/or above-defined multiples of twelve hours have elapsed; and
  a level of toxicity is attributed, which is proportional and quantitatively correlated to a level of chemical activity of the embryotoxic factors (ETFs) present in the sample of the substance.

In accordance with the present method, a classification of the sample of a substance can be defined according to the following parameterization:
  the toxicity level of the sample of a substance is defined as "toxic" when the number of dead embryos exceeds 50% of the total number of embryos placed in the verification containers;
  the toxicity level of the sample of a substance is defined as "moderately toxic" when the number of dead embryos ranges between 50% and 30% of the total number of embryos placed in the verification containers; or "non-toxic" when the number of dead embryos is less than or equal to 20% of the total number of embryos placed in the verification containers.

From the viewpoint of the operational possibilities available after the step of testing and qualitatively/quantitatively determining the toxicity level, it is possible to act upon the donor subject based on the result of the step of verifying the presence/absence of embryotoxic factors (ETFs): conveniently, the possible actions upon the donor subject can consist in exposing the donor subject to immune system-suppressing agents, for example by means of:
  infusions of immunoglobulins and/or of suppressors of cytokine production (typically intravenously);
  topical applications of progesterone and/or progesterone oil on the donor subject or on a culture medium suitable for hosting processes of artificial fertilization associated with the donor subject; and/or
  administration of vitamin or non-vitamin or nutraceutic compounds or natural and/or phytotherapeutic active ingredients as well as of other food supplements.

The invention achieves various advantages, above all in terms of optimizing the ratio between operating costs and quality of the results obtained by the tests.

In particular, the possibility of developing large quantities of "biological material", considered such in accordance with the invention, makes it possible to have, in shorter times and with reduced, economical culture spaces, a "test field" made up of a very large number of specimens that can act as "biological material", and consequently ensure faster execution times (as well a greater reliability of the toxicological tests).

Moreover, the use of so-called "biological material" according to the formal definition applied today in biological laboratory practices (rather than the use of embryos as legally classified under current legislation) allows one to avoid being subject to the complex and restrictive rules of animal experimentation, making the entire process faster and more efficient and increasing both the productivity of the laboratory and the possibility of carrying out a larger number of tests.

The method according to the present invention is thus carried out on zebrafish embryos that have developed for no more than 120 hours after fertilization (or, alternatively, medaka embryos that have developed for no more than 288 hours after fertilization or *Xenopus* embryos which cannot have developed for more than about 96 hours after fertilization), and which within this time limit are not classifiable as "animal" according to current legislation: at the same time, by using organisms belonging to the species *Danio rerio* (or similar species, such as the ones described above) it is conveniently possible to expose the live organs/systems undergoing formation to the possible presence of ETFs, thereby obtaining complete only feedback through an accurate and realistic response (which is typically obtained by an "in vivo" model).

The invention claimed is:

1. A method for suppressing an immune system of a donor subject in which embryotoxic factors (ETFs) are present comprising the following steps:
   preparing a sample of blood serum and/or plasma from the donor subject;
   associating, with the sample, a control element suitable for verifying a level of the ETFs in the sample;
   verifying the level of the ETFs in the sample based on a level of change of state of the control element, the verifying comprising the following sub-steps:
      maintaining an environmental interaction between the control element and the sample for a defined period; and
      attributing to the sample a toxicity level based on the level of change of state of the control element, the toxicity level being proportional and quantitatively correlated to a quantitative level of the ETFs in the sample; and
   exposing the donor subject to immune-system suppressing agents based on the level of change of state of the control element,
   wherein:
   the control element comprises one or more living organisms comprising at least one fish belonging to the class *Actinopterygii*, having the ability to nourish itself autonomously through one or more temporary organs associated with the living organism, and being able to supply nutritive substances to the one or more temporary organs without taking the nutritive substances from an outside environment; and
   the donor subject is a human or an animal.

2. The method according to claim 1, wherein the at least one fish is of the species *Danio rerio*.

3. The method according to claim 2, wherein the at least one fish of the species *Danio rerio* belongs to a strain of genotype "AB".

4. The method according to claim 1, wherein the one or more temporary organs comprise yolk sac temporary organs that are developed integrally with the one or more living organisms.

5. The method according to claim 1, wherein the step of associating the control element with the sample comprises the following sub-steps:
   exposing a predetermined number of the one or more living organisms to the sample, the predetermined number preferably being at least 20 embryos of *Danio rerio* having a development and/or cell multiplication time no greater than 72 hours after fertilization;
   placing groups of equal numbers of the embryos of *Danio rerio* in respective verification containers; and
   adding the sample to the verification containers.

6. The method according to claim 5, wherein the verification containers comprise at least two adjacent wells of a culture plate.

7. The method according to claim 5, wherein:
   the sub-step of maintaining an environmental interaction between the control element and the sample is carried out in the verification containers, the defined period ranging from 12 hours to 48 hours; and
   the sub-step of attributing to the sample a toxicity level is carried out by counting a number of deceased embryos after the defined period and attributing to the sample a toxicity level based on the number of deceased embryos.

8. The method according to claim 7, wherein the toxicity level is defined as "toxic" when the number of dead embryos exceeds 50% of the total number of embryos placed in the verification containers, the toxicity level being alternatively defined as "moderately toxic" when the number of dead embryos ranges between 50% and 30% of the total number of embryos placed in the verification containers, and the toxicity level being alternatively defined as "non-toxic" when the number of dead embryos is less than or equal to 20% of the total number of embryos placed in the verification containers.

9. The method according to claim 1, wherein the step of exposing the donor subject to the immune-system suppressing agents comprises administering infusions of immunoglobulin and/or suppressors of cytokine production.

10. The method according to claim 9, wherein the infusions are administered intravenously.

11. The method according to claim 1, wherein the step of exposing the donor subject to the immune-system suppressing agents comprises applying progesterone and/or progesterone oil topically on the donor subject or to a culture medium suitable for artificial insemination processes associated with the donor subject.

12. The method according to claim 1, wherein the step of exposing the donor subject to the immune-system suppressing agents comprises administering one or more of vitamin, non-vitamin, or nutraceutic compounds, natural or phytotherapeutic active ingredients, or food supplements.

* * * * *